United States Patent [19]

Galley et al.

[11] Patent Number: 5,302,767
[45] Date of Patent: Apr. 12, 1994

[54] [2.2] PARACYCLOPHANE AND AND DERIVATIVES THEREOF

[75] Inventors: Richard A. Galley, Belle Mead; Robert S. Landon, Highland Park; Kenneth C. Senior, S. Somerville, all of N.J.

[73] Assignee: Union Carbide Chemicals & Plastics Technology Corporation, Danbury, Conn.

[21] Appl. No.: 37,935

[22] Filed: Mar. 26, 1993

[51] Int. Cl.$^5$ .................. C07C 21/24; C07C 2/72; C07C 25/18
[52] U.S. Cl. ........................ 570/184; 570/183; 570/187; 585/428
[58] Field of Search .............. 570/183, 184, 187, 188, 570/201; 585/428

[56] References Cited

U.S. PATENT DOCUMENTS

| 4,532,369 | 7/1985 | Hartner | 585/428 |
| 4,675,462 | 6/1987 | Ungarelli et al. | 585/429 |
| 4,734,533 | 3/1988 | Ungarelli et al. | 570/201 |
| 4,769,505 | 9/1988 | Lee et al. | 585/428 |
| 4,783,561 | 11/1988 | Pregaglia et al. | 570/183 |
| 4,795,838 | 1/1989 | Bornengo et al. | 570/184 |
| 4,806,702 | 2/1989 | Lee et al. | 585/429 |
| 4,816,608 | 3/1989 | Bornengo et al. | 570/184 |
| 4,849,559 | 7/1989 | Lee et al. | 570/199 |
| 4,853,488 | 8/1989 | Ungarelli et al. | 570/184 |
| 4,886,923 | 12/1989 | Ungarelli et al. | 570/210 |
| 5,110,903 | 5/1992 | Lee et al. | 528/397 |

FOREIGN PATENT DOCUMENTS

| 0183083 | 6/1986 | European Pat. Off. . |
| 0220744 | 5/1987 | European Pat. Off. . |
| 0436957 | 7/1991 | European Pat. Off. . |

Primary Examiner—Warren B. Lone
Attorney, Agent, or Firm—W. K. Volles

[57] ABSTRACT

Processes are disclosed for preparing [2.2] paracyclophane and derivatives thereof by conducting the Hofmann elimination of p-methylbenzyltrimethylammonium hydroxide, or derivatives thereof, in the presence of an effective amount of oxygen to inhibit the formation of by-product polymers. The oxygen can be introduced, for example, by a purge gas stream containing molecular oxygen. Products produced by the processes are also disclosed.

20 Claims, No Drawings

[2.2] PARACYCLOPHANE AND AND DERIVATIVES THEREOF

FIELD OF THE INVENTION

The present invention relates to [2.2] paracyclophane and derivatives thereof. More specifically, the present invention relates to improved processes for preparing [2.2] paracyclophane and derivatives thereof by conducting the Hofmann elimination reaction in the presence of oxygen in order to inhibit the formation of by-product polymer.

BACKGROUND OF THE INVENTION

[2.2] paracyclophane and derivatives thereof are dimers which can be represented by the following formula:

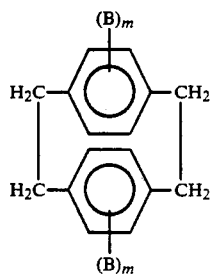

"Formula 1"

wherein B is typically hydrogen, a halogen, an alkyl, an aralkyl, or a halogen-aralkyl radical containing from 1 to about 20 carbon atoms, and m is zero or an integer from 1 to 4.

[2.2] paracyclophane (hereinafter referred to as "PCP") and its derivatives are commonly used as starting materials in the preparation of poly-p-xylylenes (hereinafter referred to as "parylene"). Parylene is often used to provide conformal coatings on a variety of substrates, such as, for example, circuit boards and electronic components, medical implant devices and surgical equipment. Typically, parylene is applied to the particular substrate by a vacuum vapor deposition technique wherein the PCP, or derivative thereof, is vaporized at an elevated temperature and polymerized directly onto the substrate to form a conformal coating of parylene.

PCP is typically prepared by reacting p-methylbenzyltrimethylammonium hydroxide (hereinafter referred to as "Q-hydroxide") in an alkaline medium via the Hofmann elimination reaction, the details of which are known to those skilled in the art. Typically, the Q-hydroxide is formed in situ by the reaction of a p-methylbenzyltrimethylammonium halide (hereinafter referred to as "Q-salt") with the alkaline medium. Thus, Q-salt is a common starting material in the preparation of PCP. Derivatives of PCP can be prepared, for example, by conducting the Hofmann elimination reaction on a corresponding derivative of Q-salt.

One problem often encountered in the preparation of PCP and derivatives thereof is that undesired products, such as trimers, other oligomers and higher polymers, can be produced as by-products (hereinafter referred to as "by-product polymers"). It is not uncommon for the yield of such by-product polymers to be greater than 5% and often greater than 10%. The term "yield" as used herein means the yield based on the stoichiometric conversion of two moles of Q-hydroxide forming one mole of PCP. Thus the yield is equal to the moles of reaction product divided by twice the moles of Q-salt or Q-hydroxide used as feed in the reaction multiplied by 100. Aside from detracting from the yield of the desired product, i.e., PCP and derivatives thereof, the formation of by-product polymers is additionally undesirable because such by-product polymers often assume a gelatinous appearance and can be difficult to separate from the reaction product.

Chemical inhibitors, such as, for example, dibenzothiazine (hereinafter referred to as "phenothiazine") have been used to inhibit polymer formation during the preparation of PCP and derivatives thereof. As used herein, the term "chemical inhibitor" means any chemical which is added to the reaction in order to inhibit the formation of by-product polymer. Other commonly used chemical inhibitors include, for example, buytlated hydroxytoluene (commonly known as "BHT"), hydroquinone and derivatives thereof. When chemical inhibitors such as described above are employed, trace amounts of the inhibitors are often present in the desired product. Trace amounts of phenothiazine can cause discoloration of the product and also can interfere with subsequent processing steps, e.g., in the chlorination of PCP. Accordingly, it is often necessary to perform purification steps in order to remove such chemical inhibitors from the PCP and derivatives thereof.

Therefore, improved processes are desired for the preparation of PCP and derivatives thereof which can inhibit the formation of by-product polymers without requiring the use of chemical inhibitors.

SUMMARY OF THE INVENTION

In accordance with the present invention, improved processes for the preparation of PCP and derivatives thereof are provided wherein the formation of by-product polymer can be inhibited by conducting the preparation in the presence of oxygen. By virtue of the present invention, it is now possible to provide a simplified process for the preparation of PCP and derivatives thereof which can have reduced by-product polymer formation without requiring the use of chemical inhibitors. In addition, the processes of the present invention can provide a reaction product comprising PCP and derivatives thereof which contains only minor amounts of by-product polymer and is substantially free of chemical inhibitors, such as, for example, phenothiazine.

In one aspect of the present invention, there is provided an improvement in a process for the preparation of PCP and derivatives thereof. The process comprises contacting at least one of Q-hydroxide, Q-salt, or derivatives thereof, with an alkaline medium in the presence of at least one solvent in a reaction vessel at conditions effective to promote the formation of a reaction product comprising PCP and derivatives thereof and a by-product polymer. The improvement to the process comprises conducting the reaction in the presence of an effective amount of oxygen to inhibit the formation of the by-product polymer.

In another aspect of the invention, there is provided a reaction product prepared in accordance with the process described above wherein the reaction product comprises at least about 90 weight % of PCP and derivatives thereof and less than about 10 weight % of by-product polymer based on the total weight of PCP, derivatives of PCP and the by-product polymer.

DETAILED DESCRIPTION OF THE INVENTION

Q-hydroxide, and derivatives thereof, are reactants in the processes of the present invention. Q-hydroxide, and certain derivatives thereof, can be represented by the following formula:

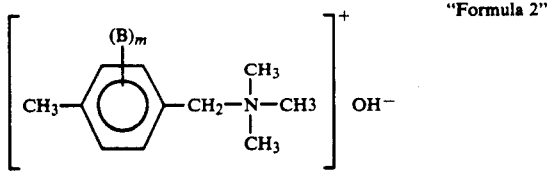

"Formula 2"

wherein B is typically hydrogen, a halogen, an alkyl, an aralkyl or a halogen-aralkyl radical containing from 1 to about 20 carbon atoms and m is zero or an integer from 1 to 4.

Preferably, Q-salt, and derivatives thereof, are used as starting materials in the processes of the present invention. Q-salt, and certain derivatives thereof, can be represented by the following formula:

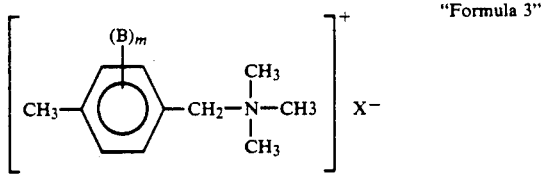

"Formula 3"

where B and m are the same as described with reference to Formula 2, and X is, preferably chlorine or bromine. When Q-salt is used as the starting material, it is preferably converted to Q-hydroxide in situ during the Hofmann elimination reaction.

Q-salt can be prepared, for example, by reacting a p-methylbenzyl halide with trimethylamine. Examples of derivatives of Q-salt include, for example, those defined by Formula 2 above, as well as those prepared by reacting p-methylbenzyl halides with other amines, such as triethylamine, tripropylamine, triphenylamine, etc. One preferred derivative of Q-salt for use in the present invention is chloro-p-methylbenzyltrimethylammonium chloride (hereinafter referred to as "CQ-salt"). CQ-salt can be prepared, for example, by chlorinating Q-salt or by reacting chloro-p-methylbenzyl-chloride with trimethylamine. The details of such reactions are known to those skilled in the art.

Q-hydroxide can be prepared, for example, by reacting Q-salt, e.g., the bromide salt, with silver oxide to precipitate the silver halide leaving Q-hydroxide in aqueous solution. The details of such reaction are known to those skilled in the art.

An alkaline medium, either organic or inorganic, is also a reactant in the processes of the present invention. Typically, the alkaline medium will be inorganic and aqueous. Preferably, the alkaline medium will be an aqueous solution of an alkali hydroxide, such as, for example, sodium hydroxide or potassium hydroxide or an aqueous solution of an alkaline earth metal hydroxide such as, for example, calcium hydroxide. As used herein, the term "solution" means a combination of a solute, e.g., alkali hydroxide, with a solvent, e.g., water, wherein the solute is at least partially dissolved in the solvent. Preferably, the aqueous solution will comprise from about 25 to 75 weight % alkali or alkaline earth metal hydroxide, and, more preferably, from about 35 to 60 weight % alkali or alkaline earth metal hydroxide based on the total weight of alkali or alkaline earth metal hydroxide and water. Mixtures of alkali and alkaline earth metal hydroxides can also be employed.

At least one solvent having solubility for the Q-hydroxide, Q-salt, or derivatives thereof, is typically also employed in the process of the present invention. Preferably, the solvents are organic solvents which are substantially immiscible with alkaline medium. Typical organic solvents include, for example, aromatics, such as toluene, alkanes, such as hexane and heptane, ethers, such as dioxane and dimethylsulfoxide (hereinafter referred to as "DMSO"), glycols and esters of glycols, e.g., dialkyl esters of mono- and polyether glycols, and mixtures thereof. DMSO is a preferred solvent for use in accordance with the present invention. Details concerning the selection and use of solvents, such as described above, are known to those skilled in the art.

Other optional ingredients may also be employed in the processes of the present invention. Typical optional ingredients include, for example, copper and iron compounds, such as cupric chloride and ferric chloride, ketones, such as acetone and imidazolidinones. Details concerning the selection and use of such optional ingredients, as well as other optional ingredients not specifically described herein, are known to those skilled in the art.

The amounts of the reactants, solvents and optional ingredients used in the processes of the present invention can be determined by those skilled in the art. Typically, the concentration of Q-salt or Q-hydroxide will range from about 2 to 50 weight %, the concentration of the alkaline medium will range from about 2 to 50 weight %, the concentration of the organic solvent will range from about 10 to 90 weight % and the concentration of water will range from about 5 to 50 weight %. A preferred reactor feed composition for use in accordance with the present invention comprises from about 50 to 60 weight % DMSO, about 10 to 15 weight % Q-salt, e.g., introduced as 20 to 30 weight % of a 50 weight % aqueous Q-salt solution, and from about 10 to 15 weight % of sodium hydroxide, e.g., introduced as 20 to 30 weight % of a 50 weight % aqueous sodium hydroxide solution.

Typically, the processes of the present invention are conducted in a batch mode in a reaction vessel, although continuous operation wherein feed materials are continuously added and products are continuously removed is within the scope of the present invention. The reaction is conducted at conditions effective to promote the formation of a reaction product comprising PCP and derivatives thereof. In general, the effective conditions suitable for use in the process of the present invention are known to those skilled in the art. Typically, the reaction pressure will be about atmospheric, i.e., from about 0.8 to 1.2 atmospheres. Typically, the reaction temperature will be from about 50° to 120° C., preferably from about 50° to 100° C., and, more preferably, from about 80° to 95° C. The reaction is preferably conducted with the feed materials, i.e., Q-hydroxide, Q-salt, and derivatives thereof, the alkaline medium and solvent, in a liquid state and with agitation. Typical reaction times range from about 0.5 to 40 hours, although reaction times of less than about 5 hours are typically preferred. The yields of PCP and derivatives thereof generally range from about 30 to 40% after a reaction time of about 4 hours and up to about 50% after a reaction time of about 24 hours.

In accordance with the present invention, the reaction is conducted in the presence of oxygen. More specifically, the Q-salt or Q-hydroxide is contacted with the alkaline medium in a reaction vessel in the presence of oxygen. It is preferred that the oxygen be introduced into the reaction vessel in a gaseous state, such as, for example, in the form of molecular oxygen or ozone, or in a liquid state, such as, for example, in the form of a peroxide. Oxygen in the form of molecular oxygen, i.e., $O_2$, is preferred for use in accordance with the present invention.

Quite surprisingly, it has been found that the presence of oxygen during the Hofmann elimination reaction can inhibit the formation of by-product polymers. Thus, in accordance with the present invention, an effective amount of oxygen is provided during the reaction in order to inhibit formation of by-product polymer. The effective amount of oxygen depends upon various factors, including, for example, the particular reaction conditions, concentration of reactants, degree of agitation, etc., and can be determined by those skilled in the art, for example, by experimentation following the guidelines set forth herein. The oxygen can be introduced into the reaction vessel prior to, or during, the contacting of the Q-salt or Q-hydroxide or derivatives thereof with the alkaline medium or during both steps. In addition, the oxygen may also be introduced into the reaction vessel after the contacting if desired. The oxygen can be provided, for example, as an oxygen atmosphere in the vapor space above the liquid feed materials or by purging the vapor space above the liquid feed materials with an oxygen-containing purge gas stream, or, preferably, by sparging, i.e., bubbling, an oxygen-containing purge gas stream through the liquid feed materials.

Preferably, the oxygen is introduced to the reaction vessel in a purge gas stream comprising from about 0.1 to 21 mole % oxygen, although higher and lower oxygen concentrations are within the scope of the present invention. More preferably, the purge gas will contain from about 1 to 10 mole % oxygen, and most preferably from about 1 to 5 mole % oxygen, with the balance comprising an inert gas, such as nitrogen. It is also preferred that the oxygen concentration be lower than the lower explosive limit of the reaction mixture. Preferably, the volumetric flow rate of the oxygen-containing purge gas stream will be from about 0.01 to 2 volumes of purge gas at standard temperature and pressure, i.e., 0° C. and 1 atmosphere, per minute, based on the internal volume of the reaction vessel. The internal volume of the reaction vessel can be determined, for example, by calculations or by measuring the volume of a liquid, e.g., water, required to fill the vessel.

In a preferred aspect of the invention, an effluent gas stream comprising an amine, e.g., trimethylamine, which may, for example, be liberated during the reaction, is discharged from the reaction vessel. The effluent gas stream is then preferably passed to a scrubbing zone wherein at least a portion of the effluent gas stream is contacted with a lean washing liquid to absorb the amine and provide a treated gas stream having a reduced concentration of the amine relative to the effluent gas stream. Preferably, the lean washing liquid comprises a p-methylbenzyl halide or derivative thereof. A rich washing liquid having an increased concentration of the amine relative to the lean washing liquid is preferably discharged from the scrubbing zone. The rich washing liquid can, for example, then be recycled, as a source of Q-salt.

Apparatus suitable for performing the processes of the present invention are conventional and may include various pieces of equipment such as, for example, pumps, compressors, reaction vessels, decanters, filters, feed tanks, product tanks, centrifuges, dryers, heat exchangers, crystallizers, scrubbers, distillation columns, and the like. Details concerning such apparatus are known to those skilled in the art.

A reaction product is produced in accordance with the present invention which typically comprises a reduced amount of by-product polymer as compared with a reaction conducted in the absence of oxygen, e.g., in a nitrogen atmosphere. Typically, the reaction product will comprise at least about 90 weight % of the combined percentages of PCP and derivatives thereof and less than about 10 weight % of the by-product polymer based on the total weight of PCP, derivatives of PCP and the by-product polymer. Preferably, the concentration of by-product polymer will be less than about 5 weight % and, more preferably, from about 0.01 weight % or less to about 3 weight %. Preferably, the reaction product is substantially free of chemical inhibitors, such as, for example, phenothiazine. As used herein, the term "substantially free" means less than about 0.1 weight %, preferably less than about 0.01 weight %, based upon the total weight of PCP, derivatives of PCP, by-product polymer and chemical inhibitors. The concentrations set forth above with respect to the reaction product are based upon the reaction product prior to any purification steps to remove PCP, derivatives of PCP, by-product polymer or chemical inhibitors from the reaction product.

The PCP and derivatives thereof can then be recovered from the reaction product by conventional means, including, for example, filtration, crystallization, washing, reflux, etc., all of which are known to those skilled in the art.

Typical derivatives of PCP prepared in accordance with the processes of the present invention include, for example, dichloro-[2.2]-paracyclophane, tetrachloro-[2.2]-paracyclophane, tetramethyl-[2.2]-paracyclophane, dimethyldichloro-[2.2]-paracyclophane, diethyl-[2.2]-paracyclophane, dibromyl-[2.2]-paracyclophane, etc. Preferred derivatives of PCP include, for example, 5,11-dichloro-[2.2]-paracyclophane, 5,12-dichloro-[2.2]-paracyclophane, 5,13-dichloro-[2.2]-paracyclophane, 5,14-dichloro-[2.2]-paracyclophane and mixtures thereof.

In addition to preparing halogenated derivatives of PCP, such as dichloro-[2.2]-paracyclophane, by the Hofmann elimination of CQ-salt as described above, the halogenated derivatives can also be prepared by chlorinating PCP. The details concerning the chlorination of PCP are known to those skilled in the art.

PCP and derivatives thereof can be used, for example, as raw materials in the preparation of parylene. As noted above, parylene is commonly used to provide conformal coatings on a wide variety of substrates. Typical substrates used in the electronics industry often coated with parylene include, for example, circuit board, electronic components, magnetic coil windings, and the like. Typical substrates used in the medical industry often coated with parylene include, for example, surgical implants, such as pacemakers, and surgical tools, such as septums, catheters, and the like. Parylene is also used, for example, in the preservation of books, historical artifacts, insects, currency, etc.

The following examples are provided for illustrative purposes and are not intended to limit the scope of the claims which follow.

The ingredients used in the examples are common chemicals readily available in the chemical industry.

EXAMPLE 1

Q-salt Preparation

Q-salt was prepared by charging 3500 grams (g) of p-methylbenzyl chloride to a round bottomed flask equipped with a cooling jacket. 6058 g of 25 weight % aqueous trimethylamine was added slowly, while agitating the flask contents. The reaction temperature was kept below 50° C. by regulating the rate of the trimethylamine feed. The reaction was considered complete once the lower organic phase of p-methylbenzyl chloride could no longer be seen.

EXAMPLE 2

CQ-salt Preparation

2(3)chloro-p-methylbenzyl chloride was prepared by charging 5432.3 g of 2 chloro-p-xylene, 116.8 g pyridine and 5.4 g of VAZO-64 catalyst to a 12 l round bottomed flask. VAZO-64 catalyst is a 2,2'-azobis-2-methylproprionitrile catalyst, available from E. I. DuPont de Nemours and Company, Wilmington, Del. The flask temperature was raised to 70° C. Chlorine in the form of about 100% gaseous chlorine was introduced at a rate of around 1 g/min. The reaction temperature was maintained between 70° and 80° C. by adjusting the flowrate of the chlorine. Nitrogen gas was used to purge the head space. The reaction was judged to be complete when the impurity level (other chlorinated species) reached around 10% of the level of 2(3)chloro-p-methylbenzyl chloride. A total of 1007 g of chlorine had been added. A small amount of white solids (water soluble) suspended in the liquid was allowed to settle and the liquid layer was decanted off. The liquid was recharged to the flask once the solids had been removed. The reaction product was distilled under 15 millimeters of vacuum. Unreacted chloro-p-xylene was recovered at 61° C. 1984.8 g of 2(3)chloro-p-methylbenzyl chloride was recovered at 70° C. The purity was 95%. CQ-salt was prepared by charging 300 g of 2(3)chloro-p-methylbenzyl chloride to a round bottomed flask equipped with a cooling jacket. 447 g of 25 weight % aqueous trimethylamine was added slowly, while agitating the flask contents. The reaction temperature was kept below 50° C. by regulating the rate of the trimethylamine feed. The reaction was considered complete once the lower organic phase of 2(3)p-methylbenzyl chloride could no longer be seen.

COMPARATIVE EXAMPLE A

PCP Preparation with Nitrogen 326 g of DMSO was heated to 85° C. in a 1 liter (1) baffled, glass resin kettle. 160 g of 50 weight % aqueous sodium hydroxide was added, and the reactor contents allowed to return to 85° C. 120 g of 50 weight % aqueous Q-salt solution, as prepared in accordance with Example 1, was added over a period of 1 minutes. The reactor contents were then maintained at 85° C. for a further 25 hours. Throughout this period, a nitrogen atmosphere was maintained over the reaction mixture.

At the end of the reaction period, finely dispersed, off-white solids had formed. These were collected by filtration, washed with water, and then refluxed in 400 milliliters (ml) toluene for 60 minutes. The resulting solution was filtered while still hot to remove the undissolved polymer. The toluene was allowed to cool and the resulting crystals were recovered by filtration. A second crop of crystals was taken by stripping toluene, allowing the remaining solution to cool and recovering the resulting crystals by filtration. The resulting solids were washed with acetone and dried in an oven, yielding 11.7 g of PCP (37% yield) as white crystals. 3.0 g (9.6% yield) of polymer were recovered.

The calculations to determine yield were as follows:

1) $\% \text{ Yield of PCP} = \frac{100 \times \text{weight of PCP obtained}}{(\text{weight of PCP assuming complete conversion of Q-salt})}$ a) weight of PCP assuming complete conversion of Q-salt
$= \frac{\text{weight of Q-salt}}{\text{mol. wt Q-salt}} \times \frac{\text{mol. wt PCP}}{(\text{mols of Q-salt to make 1 mol PCP})}$ $= \frac{60 \text{ g}}{199.4} \times \frac{208}{2} = 31.3 \text{ g}$ $\% \text{ Yield of PCP} = 100 \times \frac{11.7 \text{ g}}{31.3 \text{ g}} = 37\%$ 2) $\% \text{ Yield of polymer} = \frac{100 \times \text{weight of polymer obtained}}{(\text{weight of polymer assuming complete conversion of Q-salt})}$ a) weight of polymer assuming complete conversion of Q-salt
$= \frac{\text{weight of Q-salt}}{\text{mol. wt Q-salt}} \times \frac{(\text{mol. wt repeat unit } (C_8H_8))}{}$ $= \frac{60 \text{ g}}{199.4} \times 104 = 31.3 \text{ g}$ $\% \text{ Yield of polymer} = 100 \times \frac{3 \text{ g}}{31.3 \text{ g}} = 9.6\%$

EXAMPLE 3

PCP Preparation with Air Atmosphere 326 g of DMSO was heated to 85° C. in a 1 l baffled, glass resin kettle. 160 g of 50 weight % aqueous sodium hydroxide was added, and the reactor contents were allowed to return to 85° C. 120 g of 50 weight % aqueous Q-salt solution, as prepared in accordance with Example 1, was added over a period of 1 minute. The reactor contents were then maintained at 85° C. for a further 25 hours. Throughout this period, the reaction mixture was left exposed to the air.

At the end of the reaction period, finely dispersed, off-white solids had formed. These were collected by filtration, washed with water, and then refluxed in 400 ml toluene for 60 minutes. The resulting solution was filtered while still hot to remove the undissolved polymer. The toluene was allowed to cool and the resulting crystals were recovered by filtration. A second crop of crystals was taken by stripping toluene, allowing the remaining solution to cool and recovering the resulting crystals by filtration. The resulting solids were washed with acetone and dried in an oven, yielding 15.3 g of PCP (51% yield) as white crystals. 0.6 g (2.0% yield) of polymer were recovered.

EXAMPLE 4

PCP Preparation with Air Sparge 3848 g of DMSO were heated to 85° C. in a 12 l stirred tank reactor. 960 g sodium hydroxide pellets, 810 g of distilled water and 1600 g of 42.3 weight % aqueous Q-salt solution, prepared in accordance with Example 1, were added. The reactor contents were then maintained at 85° C. for a further 4 hours. Throughout this period, the reaction mixture was sparged with air at a flow rate of 400 ml per minute.

91.2 g of PCP (25.8% yield) and 3.3 g (0.9% yield) of polymer were obtained following the recovery method described in Example A.

EXAMPLE 5

PCP Preparation with Oxygen Sparge 42.6 kilograms (kg) of DMSO were heated to 85° C. in a 30 gallon stirred tank reactor. 21.3 kg of 50 weight % aqueous sodium hydroxide and 15.9 kg of 50 weight % aqueous Q-salt solution, prepared in accordance with Example 1, were added. The reactor contents were then maintained at 85° C. for a further 4 hours. Throughout this period, the reaction mixture was sparged with 2 mol % oxygen in nitrogen mixture at a flow rate of 2 l per minute.

1347 g of solids were filtered from the reaction mixture. 150.5 g of these solids were taken for PCP recovery, following the method described in Example A. 125.2 g of PCP (28% yield) and 7 g (1.6% yield) of polymer were obtained.

EXAMPLE 6

Chloride Derivative of Q-Salt 5230 g of 50 wt. % aqueous Q-salt solution prepared in accordance with Example 1 was added to a 12 liter glass, baffled flask. The reactor contents were heated to 35° C. 720 g of chlorine gas were sparged into the liquid over a period of 10 hours, while maintaining the temperature of the reactor contents between 40° and 45° C. The reactor product comprised primarily water and chlorinated derivatives of Q-Salt.

COMPARATIVE EXAMPLE B

Chloride Derivative of PCP with Nitrogen 460 g of toluene, 80 g of 50% aqueous sodium hydroxide, 78 g of DMSO, and 0.1 g of sodium borohydride were charged to a 1 l, baffled resin kettle. This mixture was well mixed and heated to 85° C. under nitrogen. Then 46 g of a 50% aqueous CQ-salt solution, prepared in accordance with Example 2, were added at 3.1 ml/hour while the reaction mixture was maintained under a nitrogen atmosphere. At the end of the addition, the mixture was heated at 85° C. for an additional 12 hours.

The aqueous and DMSO phases were separated and the toluene layer containing the product was washed with water and evaporated. The residue was taken up in acetone and cooled to yield 7.1 g (52% yield) of white polymer. Only 1.5 g of the chloride PCP derivative were produced, corresponding to an 11% yield.

EXAMPLE 7

Chloride Derivative of PCP with Air 460 of toluene, 80 g of 50% aqueous sodium hydroxide, 78 g of DMSO, and 0.1 g of sodium borohydride were charged to a 1 l, baffled resin kettle. This mixture was well mixed and heated to 85° C. under air. Then 46 g of a 50% aqueous CQ-salt solution, prepared in accordance with Example 2, were added at 3.1 ml/hour while the reaction mixture was maintained under an air atmosphere. At the end of the addition, the mixture was heated at 85° C. for an additional 12 hours.

The resulting reaction mixture contained no visible polymer. The aqueous and DMSO phases were separated and the toluene layer containing the product was washed with water and evaporated. The residue was taken up in acetone and cooled to yield 5.0 g of the chloride PCP derivative (36.5% yield) as white crystals. No polymer was recovered.

EXAMPLE 8

PCP Preparation with air with trimethylamine recovery 400 g of DMSO were heated to 95° C. in a 1 l baffled, glass resin kettle. 100 g of 50 weight % aqueous Q-salt solution, prepared in accordance with Example 1, were added over a period of 1 minute and the reactor contents were allowed to return to 95° C. under an air atmosphere. 120 g of 50 weight % aqueous sodium hydroxide was added slowly over a 4 hour period, whilst the reactor contents were maintained at 95° C.

Gases which evolved during the reaction were allowed to escape from the reactor through a water cooled condenser. The gas exiting from the condenser was bubbled into a 150 ml graduated flask containing 82.5 g of p-methylbenzylchloride and 20 g water. Once the reaction of Q-salt to PCP had been stopped the reaction mixture was sparged with air for 10 hours, and the effluent gases were bubbled into the flask containing p-methylbenzylchloride and water.

The solids were recovered from the glass resin kettle in accordance with the method in Example A, yielding 11.7 g of PCP (45% yield) as white crystals. 0.07 g (0.27% yield) of polymer were recovered.

The aqueous layer from the graduated flask was recovered by decanting it from the remaining p-methylbenzylchloride. The water was stripped under vacuum at 95° C. The Q-salt solids obtained were dried in a vacuum oven overnight at 70° C. 29 g of Q-salt crystals were recovered, equivalent to 58% of the Q-salt originally charged to the glass resin kettle.

Although the invention has been described with reference to specific aspects, those skilled in the art will recognize that other variations are possible within the scope of the claims that follow. For example, derivatives of Q-salt or Q-hydroxide, other than specifically disclosed herein, may be used to prepare derivatives of PCP within the scope of the invention.

We claim:

1. In a process for the preparation of {2.2}-paracyclophane or derivatives thereof selected from the group consisting of dichloro-{2.2}-paracyclophane, tetrachloro-{2.2}-paracyclophane, tetramethyl-{2.2}-paracyclophane, dimethyldichloro-{2.2}-paracyclophane, diethyl-{2.2}-paracyclophane and dibromyl-{2.2}-paracyclophane comprising contacting at least one of p-methylbenzyltrimethylammonium hydroxide, p-methylbenzyltrimethylammonium halide, or derivatives thereof, with an alkaline medium in the presence of at least one solvent in a reaction vessel at a temperature of from about 50° to 120° C. to promote the formation of a reaction product comprising the {2.2}-paracyclophane or said derivatives thereof and a by-product polymer; the improvement which comprises conducting said contacting in the presence of an effective amount of oxygen to inhibit the formation of the by product polymer.

2. The process of claim 1 wherein the yield of the by-product polymer is less than about 5.0%.

3. The process of claim 1 wherein oxygen is introduced by passing a purge gas stream comprising oxygen into the reaction vessel during said contacting.

4. The process of claim 3 wherein the purge gas stream comprises from about 0.1 to 21 mole % oxygen.

5. The process of claim 4 wherein the purge gas stream comprises from about 1 to 10 mole % oxygen.

6. The process of claim 3 wherein the purge gas stream is introduced at a flow rate of from about 0.01 to 2 volumes of purge gas per minute based on the internal volume of the reaction vessel.

7. The process of claim 3 wherein the purge gas stream is introduced to the reaction vessel substantially continuously during said contacting.

8. The reaction product prepared in accordance with the process of claim 1, said reaction product comprising at least about 90 weight % of the {2.2}-paracyclophane and said derivatives thereof and less than about 10 weight % of the by-product polymer based on the total weight of {2.2}-paracyclophane, said derivatives of {2.2}-paracyclophane and by-product polymer.

9. The reaction product of claim 8 comprising from about 0.01 to 3 weight % of the by-product polymer based on the total weight of {2.2}-paracyclophane, said derivatives of {2.2}-paracyclophane and the by-product polymer.

10. The reaction produce of claim 8 wherein said derivatives of {2.2}-paracyclophane are selected from the group consisting of 5,11-dichloro-{2.2}-paracyclophane, 5,12-dichloro-{2.2}-paracyclophane, 5,13-dichloro-{2.2}-paracyclophane, 5,14-dichloro-{2.2}-paracyclophane and mixtures thereof.

11. The reaction product of claim 8 which is substantially free of chemical inhibitors.

12. A process for the preparation of {2.2}-paracyclophane or derivatives thereof selected from the group consisting of dichloro-{2.2}-paracyclophane, tetrachloro-{2.2}-paracyclophane, tetramethyl-{2.2}-paracyclophane, dimethyldichloro-{2.2}-paracyclophane, diethyl-{2.2}-paracyclophane and dibromyl-{2.2}-paracyclophane comprising, contacting at least one of p-methylbenzyltrimethylammonium hydroxide, p-methylbenzyltrimethyl-ammonium halide, or derivatives thereof, with an alkaline medium and at least one solvent in a reaction vessel at a temperature of from about 50° to 120° C. to promote the formation of a reaction product comprising {2.2}-paracyclophane or said derivatives thereof, wherein said contacting is conducted in the presence of an effective amount of oxygen to inhibit the formation of by-product polymer.

13. The process of claim 12 wherein the derivative of [2.2]-paracyclophane is dichloro-[2.2]-paracyclophane.

14. The process of claim 13 wherein the derivative of p-methylbenzyltrimethylammonium halide is chloro-p-methylbenzyltrimethylammonium chloride.

15. The process of claim 14 wherein the chloro-p-methylbenzyltrimethylammonium chloride is prepared (i) by reacting chloro-p-methylbenzyl chloride with trimethylamine or (ii) by chlorinating p-methylbenzyltrimethylammonium chloride.

16. The process of claim 12 wherein oxygen is introduced by passing a purge gas stream comprising oxygen into the reaction vessel during said contacting.

17. The process of claim 16 wherein the reaction product further comprises an amine.

18. The process of claim 17 further comprising withdrawing an effluent gas stream comprising the amine from the reaction vessel.

19. The process of claim 18 further comprising contacting at least a portion of the effluent gas stream with a lean washing liquid to provide a treated gas stream having a reduced concentration of the amine relative to the effluent gas stream.

20. The process of claim 19 wherein the lean washing liquid comprises p-methylbenzyl halide and the amine is trimethylamine.

* * * * *